United States Patent [19]

Nokihara et al.

[11] Patent Number: 5,356,596
[45] Date of Patent: Oct. 18, 1994

[54] APPARATUS FOR ISOLATION OF SYNTHETIC PEPTIDE WITHOUT MECHANICAL LOSS

[75] Inventors: Kiyoshi Nokihara; Rintaro Yamamoto; Shin Nakamura, all of Kyoto, Japan

[73] Assignee: Shimadzu Corporation, Kyoto, Japan

[21] Appl. No.: 22,036

[22] Filed: Feb. 24, 1993

[30] Foreign Application Priority Data

Feb. 28, 1992 [JP] Japan .................. 4-043312

[51] Int. Cl.$^5$ .................. C08F 2/00; B01L 3/00; C12M 1/00
[52] U.S. Cl. .................. 422/131; 422/99; 422/101; 935/87; 935/88; 435/287
[58] Field of Search .................. 422/131, 116, 62, 99, 422/101, 68.1; 436/86, 89, 177, 178, 179, 180; 239/526, 390, 391; 935/87, 88; 435/287

[56] References Cited

U.S. PATENT DOCUMENTS

| | | | |
|---|---|---|---|
| 3,557,077 | 1/1971 | Brunfeldt et al. | 935/88 X |
| 3,700,174 | 10/1972 | Beck | 239/526 |
| 3,777,981 | 12/1973 | Probst et al. | 239/526 X |
| 4,362,699 | 12/1982 | Verlander et al. | 422/131 |
| 4,483,964 | 11/1984 | Urdea et al. | 422/131 X |
| 4,598,871 | 7/1986 | Hartle | 239/706 |
| 4,746,490 | 5/1988 | Saneii | 422/62 |
| 4,766,082 | 8/1988 | Marteau D'Autry | 436/178 |
| 4,775,629 | 10/1988 | Kuhl et al. | 435/299 |
| 4,850,536 | 7/1989 | Teranishi et al. | 239/526 X |
| 5,019,348 | 5/1991 | Ohms et al. | 422/63 |
| 5,055,272 | 10/1991 | Wheeler et al. | 422/133 |
| 5,170,940 | 12/1992 | Salber et al. | 239/135 |
| 5,288,464 | 2/1994 | Nokihara | 422/101 |

FOREIGN PATENT DOCUMENTS

0425297A2 5/1991 European Pat. Off. .
3723004A1 1/1989 Fed. Rep. of Germany .
808872 2/1989 Fed. Rep. of Germany .

OTHER PUBLICATIONS

Cole–Palmer Products Catalog, 1993–1994, p. 829, 1992.

*Primary Examiner*—Robert J. Warden
*Assistant Examiner*—Christopher Y. Kim
*Attorney, Agent, or Firm*—Nikaido, Marmelstein, Murray & Oram

[57] ABSTRACT

In connection with an automated peptide synthesizer, an apparatus and associated method through which peptides produced in simultaneous multiple synthesis are together isolable. Cleavage to liberate the peptides from linkage to the support matrix of the solid phase is carried out in the same vessels in which the synthesizing reactions took place. Prior to cleavage, a drainage port of each reaction vessel is closed off by a cap. The reaction vessel is inserted into a centrifuge tube, which in turn is put into a rack supporting a number of tubes equal to the number of channels of the peptide synthesizing apparatus. After the peptides are cleaved and dissolved into cleaving solution added into each of the reaction vessels, the caps are removed from the drainage ports of each reaction vessel, and the vessel is returned into the centrifuge tube. A plastic jet-fitting attached to the nozzle tip of a blow unit pressure gun is inserted into and pressed into contact against the supply opening of the reaction vessel. Operating a trigger of the pressure gun releases pressurized inert gas into the reaction chamber. The peptide-dissolved cleaving solution is thereby passed through the drainage port, and is thus transferred in liquid phase into the centrifuge tube as filtrate. Associated with the blow unit pressure gun, a needle tube fitting is provided for localized desiccation of wetted peptide following precipitation and centrifuging.

5 Claims, 3 Drawing Sheets

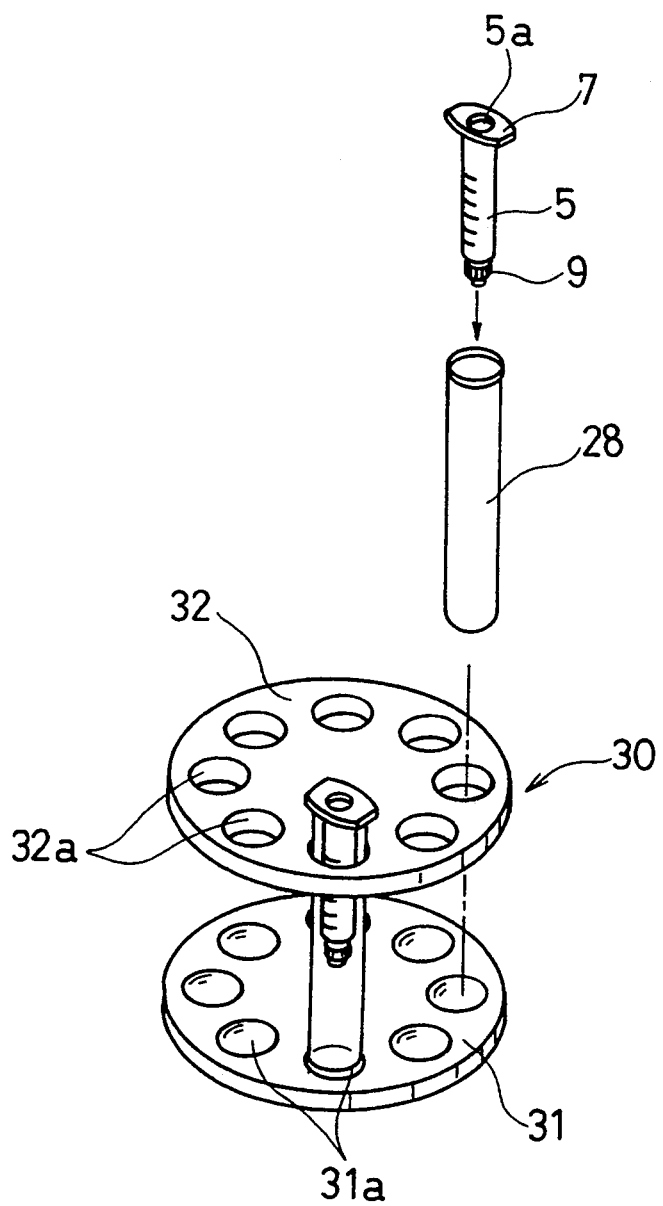

APPARATUS FOR ISOLATION OF SYNTHETIC PEPTIDE WITHOUT MECHANICAL LOSS

BACKGROUND

1. Technical Field

Solid-phase peptide synthesis is a general basis of the inventive technology disclosed in the following, which more specifically relates to an apparatus employed in the isolation of synthesized peptides through cleavage from the insoluble support matrix of the solid phase, and furthermore to an associated method, facilitated by the apparatus, through which peptides produced in simultaneous multiple synthesis are together isolable, for recovery in final product form.

2. Description of the Background

Simultaneous multiple peptide synthesis is becoming of significantly increasing importance for the rapid screening or evaluation of peptides such as epitopes, agonists, antagonists or more potent structures. An eight-channel automated simultaneous solid phase peptide synthesizer has been manufactured, and has wide flexibility for syntheses. The apparatus has eight reaction vessels, each having a drainage port through which washing solvents are flushed, eight micro-syringes and an amino acid station for 160 amino acid vials. The eight independent channels allow cross-contamination-free syntheses and the generation of variable amounts of high quality peptides.

The flexibility of the automated peptide synthesizer enables the simultaneous production of peptides of different length, which can be produced according to different chemical protocols, as well as the simultaneous synthesis of different peptides. The instrument can therefore be used for the rapid evaluation of peptide synthetic chemistry or formation reaction conditions, and moreover for studies of epitopes or structure-activity relationships.

The automated peptide synthesis comprises basic amino-acid coupling cycles, wherein the carboxyl-terminal ends of peptide chains of amino acid residues coupled in synthesis are linked to styrene or other polymeric particulate beads, which can be resin coated, serving as a support matrix. The $\alpha$-amino group of each amino acid added for coupling during synthesis must be protected, (i.e. blocked), so that only its activated carboxyl end is reactive (usual side groups of the amino acids are commonly protected as well). Because the compound serving as a protecting group joins to the nitrogen in the $\alpha$-amino group, this may be termed "N-$\alpha$ protecting." The $\alpha$-amino group of the terminal residue last coupled onto the growing peptide chain (or initially linked to the support matrix) is thus in a protected state and must therefore be "deprotected" prior to a subsequent coupling reaction.

Generally in the end of a coupling cycle, the elongating peptide chains are washed in solvent to cleanse them of residual coupling reagents and byproducts of the prior coupling reaction. The N-terminus away from the linked end of the peptide chain is then prepared for coupling by chemically removing the N-$\alpha$ protecting group; and, following another washing, a coupling reagent containing the next protected amino acid (i.e., having the N-$\alpha$ blocking group attached) to be joined to the deprotected N-$\alpha$ end of the peptidyl resin is added. Subsequent to this step, which produces amino-terminal end protected peptidyl resin intermediate in synthesis, is yet another washing in solvent, completing a normal coupling cycle in the peptide synthesis, which may be repeated to obtain a peptide product having a desired amino acid sequence.

Following the coupling cycles of a peptide synthesizing procedure in the peptide synthesizer, a final cycle ensues. Normally, after the protecting groups on the N-$\alpha$ ends of the peptidyl resin have been removed as prior to coupling, the synthesized, resin-linked peptides are cleansed with a final sequence of washing solvents. Alternatively, depending upon the desired application of the synthesized peptide product in final form, the peptidyl resin prior to final washing can be left in its protected state; and, given the chemistry of the protecting groups, the product can remain that way throughout the isolation process. The washed peptide product is then dried by inert gas blown through a supply opening into a reaction chamber of each reaction vessel, which contains the peptidyl resin on a filter.

In order to obtain a final peptide product, the synthesized peptides must be isolated, through cleavage From the support matrix, in a process which is carried out apart from the peptide synthesizer. This process generally requires that the peptidyl resin, i.e., the peptide in its insoluble solid phase Following synthesis, be manually transferred into a separate container, wherein it is treated with a cleaving solution which liberates the peptides from linkage to the support matrix. The resulting peptidyl solution is further isolated into final product form through a common extraction method, viz., precipitation and centrifuging.

The manually performed inter-vessel transfer of the peptidyl resin or resin-liberated peptidyl solution to containers in which the cleavage reaction or the final product extraction is carried out gives rise to mechanical loss, i.e. the tendency for some of the peptidyl resin or solution to remain behind in the vessel from which it was transferred (by pouring, for example). This consequently can reduce peptide yields, particularly in the case of simultaneous multiple peptide synthesis; moreover, the peptides are thus susceptible to contamination in the isolation process.

SUMMARY

It is desirable to improve the efficiency of the peptide isolation procedure overall; In particular to eliminate mechanical losses resulting from inter-vessel transfer of peptidyl resin or peptidyl solution, further to ensure accuracy in micro-mole regulation of small-scale peptide synthesis.

In a synthesized peptide isolation apparatus of the present invention, the reaction liberating the peptidyl resin, wherein the resin support matrix is suspended in the cleaving solution in which the peptide elongate chains cleaved from the resin become soluble, is carried out in the same reaction vessels in which the peptides are synthesized. Each reaction vessel is substantially cylindrical and retains a filter at a gap over a drainage port projecting from an end of the vessel. The region above the filter which it defines together with the reaction vessel wall is a reaction chamber. The reaction vessel drainage port is plugged or closed off by a stopper, or cap. Cleaving solution is then added directly to the synthesized peptidyl resin resting on the filter in the reaction chamber. With the drainage port capped off, pressure balance is such that surface tension of the meniscus of peptidyl cleaving solution just entering the port is maintained, restraining the solution from travelling further.

With the synthesized peptide thus dissolved into in a liquid phase, the solution is transferred to a centrifuge tube in which it is precipitated out, then centrifuged and dried. The transfer of the peptidyl solution is impelled by pressurized inert gas introduced into the reaction chamber by an inventive blow unit, which completely expels the peptidyl solution through the drainage port and into the centrifuge tube.

Accordingly, a method of isolating peptides synthesized in the reaction vessels, which correspond to channels of a solid-phase peptide synthesizing apparatus, is as follows.

Initially, the drainage port to the reaction chamber is plugged by the stopper. The reaction vessel, which has a flanged reaction solution supply opening, is then inserted into a centrifuge tube, wherein it is retained by the flange resting on the centrifuge tube rim. The centrifuge tube is in turn put into a rack capable of supporting at least a number of tubes equal to the number of channels of the solid-phase peptide synthesizing apparatus, such that peptide-isolation can be carried out simultaneously from that number of reaction vessels.

Cleaving solution is added into the reaction chamber therein containing synthesized peptidyl resin, i.e. peptide chains linked to the insoluble support matrix. Therein, the N-α amino groups at time N-terminuses (often as well as side chains) of the peptides can be left protected, or in other procedures, they are deblocked. The plugged reaction vessels thus are left standing in the rack until enough time has passed to allow the reaction cleaving the peptides from the resin to take place, and until the peptides become soluble into the cleaving solution.

Each reaction vessel is then briefly withdrawn from the centrifuge tube, the stopper is detached from the drainage port, and the vessel is returned into the centrifuge tube. Subsequently, the nozzle of a blow unit pressure gun is inserted into and pressed into contact against the supply opening of the reaction vessel, wherein a plastic jet-fitting attached to the nozzle tip seals the contact. Operating a trigger of the pressure gun releases inert gas into the reaction chamber under pressure regulated by a pressure governor in a main body of the blow unit. Tile peptide-dissolved cleaving solution is thereby passed via the filter through the drainage port, and is thus transferred into the centrifuge tube as filtrate. Therein, the resin support remains on the filter in the reaction chamber.

To precipitate the peptide, ether (diethylether) is added to the peptidyl solution in the centrifuge tube. Isolation of the final peptide product is then completed by centrifuging and subsequently decanting the supernatant. However, at this point the peptide precipitate remains wet with the precipitating agent, and if left to dry by evaporation only, it is subject to oxidation or other contamination. Therefore, associated with the blow unit pressure gun, a needle tube fitting is provided for blowing a stream of desiccating inert gas on the wet peptide precipitate. One end of the needle tube is configured to be interchangeable with the jet-fitting connected to the nozzle of the pressure gun, and the end opposite is tapered in order to focus the pressurized inert gas effluent from the needle tube. When the pressure gun trigger is activated to open the nozzle valve, a stream of pressurized inert gas is introduced within the centrifuge tube, wherein it can be directed to locally dry the peptide product. Thus the wet precipitate is rapidly dried without peptidyl loss.

As simultaneous peptide cleavage using the same reaction vessels can be readily performed, mechanical loss at the cleavage stage is minimized or eliminated, even in small-scale syntheses. Furthermore, the nitrogen atmosphere issuing from the blow unit as the peptidyl solution is expelled into the centrifuge tube, and again as the peptide precipitate is dried, helps to prevent oxidation of the peptide product, and removes scavenger which has cleansed the peptide product of non-peptidyl material.

The foregoing and other objects and advantages will be more fully apparent from the following detailed description, which, together with the drawings, is illustrative of the preferred embodiment of the present invention, without intending to be restrictive of such modifications as might become apparent to persons skilled in this art.

BRIEF DESCRIPTION OF THE DRAWINGS

FIG. 4 is an exploded perspective view of peptide isolation apparatus, showing arrangement prior to a cleaving process.

DETAILED DESCRIPTION

Figure 1:
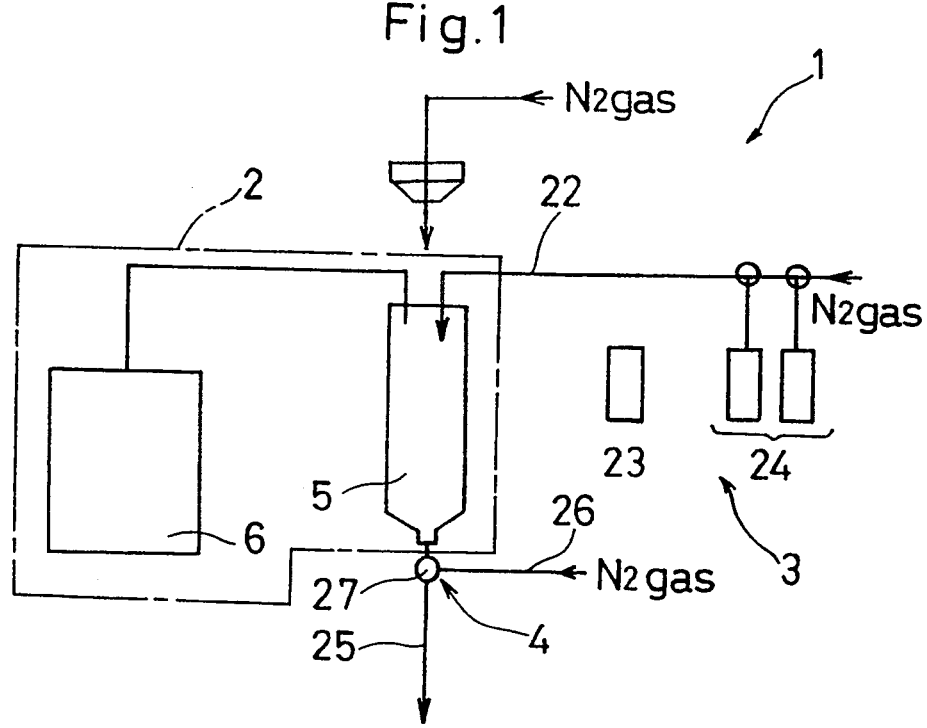
FIG. 1 is a schematic diagram Illustrating a reaction assembly in a solid phase peptide synthesizing apparatus, and indicating the associated blow unit.

FIG. 1 schematically illustrates basic components of a reaction assembly 1 in a solid-phase peptide synthesizing machine, and further shows an associated peptide isolation apparatus 2 of the preferred embodiment according to the present invention. The reaction assembly 1 comprises a reaction vessel 5, a reagent/solvent supply station 3, and a drainage device 4.

The reaction vessel 5 is removable and is employed in the isolation apparatus 2; it is thus used both for the solid phase peptide synthesis producing protective (protected by N-α groups) peptidyl resin (or alternatively, N-α deprotected peptidyl resin), and for the subsequent cleavage process which liberates the peptides, wherein they can become solute in the cleaving solution. The isolation apparatus 2 also comprises an inventive blow unit 6.

Figure 2:
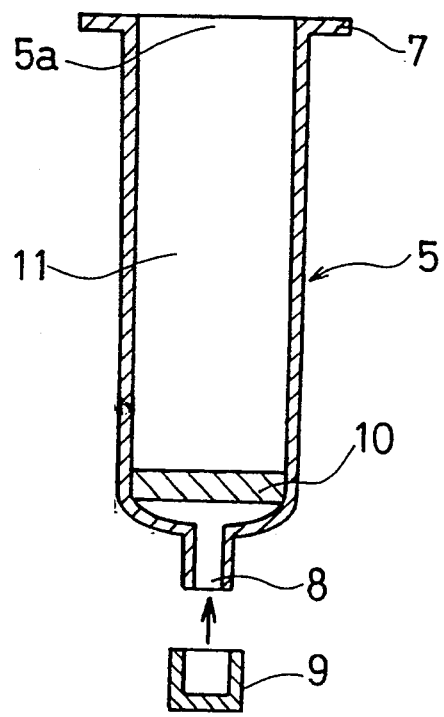
FIG. 2 is a cross-sectional view of a reaction vessel employed in the preferred embodiment of the present invention.

As shown in FIG. 2, the reaction vessel 5 is substantially a cylinder in form, one end of which is a reagent-/washing-solvent supply opening 5a rimmed by a flange 7, and projecting from the other end of which is a nipple-shaped drainage port 8. The drainage port 8 is tapered, or can lave an external groove or grooves, such that it is sealable by a liquid-tight cap 9 having a corresponding tapered bore, or corresponding internal groove(s). The reaction vessel 5 is made of a substance which is not chemically reactive with the insoluble support matrix, described in the following, and which scarcely generates static electricity. Polypropylene resin is an example of a suitable material which is inexpensive, and its non-specific adsorbency of synthesized peptide is minimal.

The interior of the reaction vessel 5 is divided by a filter 10 located at a gap over the drainage port 8. A reaction chamber 11 is defined by the bore of the reaction vessel and the peptidyl-resin retaining surface of the filter 10. The filter 10 is made from a suitable porous material, e.g. from such polymeric materials as polyalkylene resin, including polypropylene or polyethylene resin. Herein polypropylene resin is the most preferable material for the filter 10.

Figure 3:
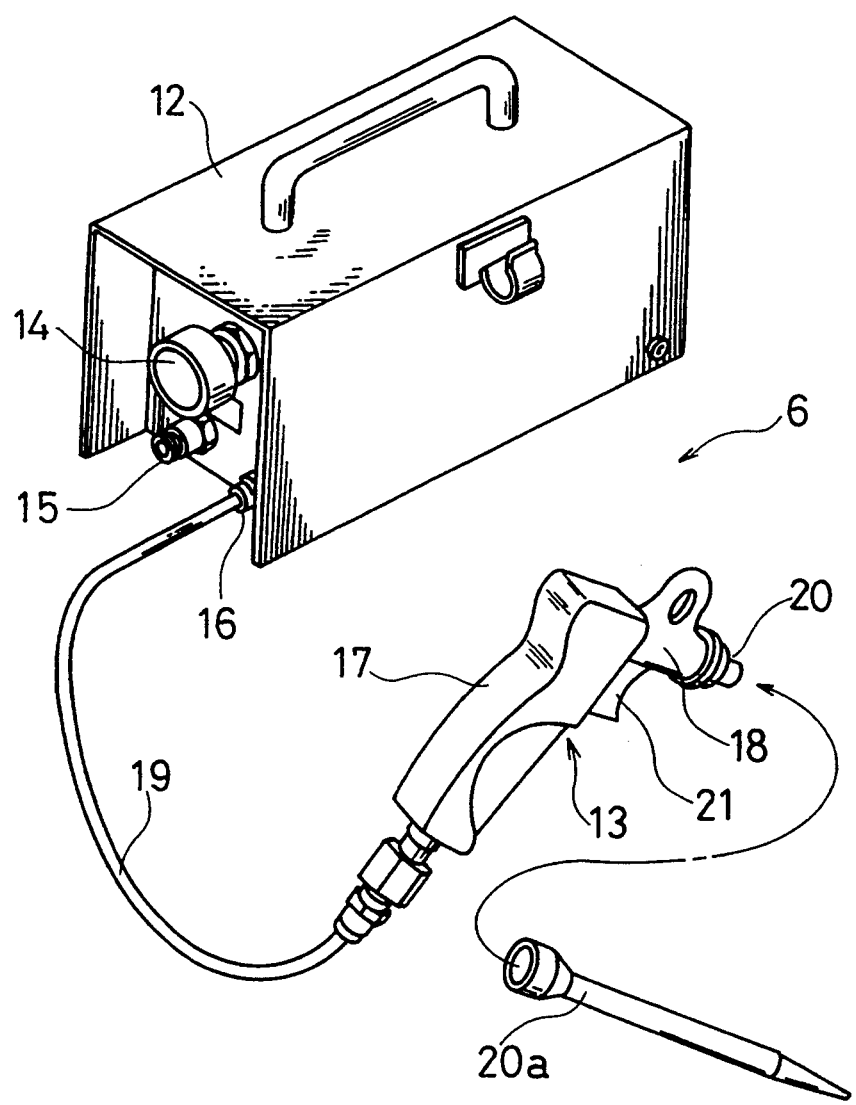
FIG. 3 Is a perspective view of the inventive blow unit.

Referring to FIG. 3, the blow unit 6 is shown to principally comprise a main body 12, incorporating a (not shown) pressure governor, and a pressure gun 13. The pressure governor is adjustable through a controller 14 mounted into the main body 12 exterior, together with an inlet 15 and an outlet 16. The inlet 15 is connected with a (not shown) nitrogen gas source, which can be through communication with a gas supply line (connected to a nitrogen gas bomb) of the peptide synthesizing machine. A grip 17 of the pressure gun 13 contains a gas flow passage, and connected to the gas flow passage entrance at the base of the grip 17 is a hose 19, further connected to the outlet 16. In communication with the gas flow passage at its exit is a nozzle 18. The nozzle 18 expels inert gas delivered under controllably regulated pressure from the main body 12. A plastic (rubber in the preferred embodiment) jet-fitting 20 is connected to the nozzle 18, and forms an airtight seal when inserted into the reaction chamber 11 and pressed against the rim of the reaction vessel 5 supply opening 5a. A trigger 21 mounted on the grip is activated to open and close a valve to the nozzle 18. The rubber jet-fitting 20 Is interchangeable with a needle tube fitting 20a, employed for post-centrifuge drying of ether-wetted peptide precipitate.

The reagent/solvent supply station 3 comprises a supplier assembly 22 which supplies coupling reagents or washing solvent through communication with the supply opening 5a of each reaction vessel 5. A plurality of reagent tanks 24 are provided for introduction into the supplier assembly 22 of the N-α deprotecting reagent for supply to deblock the peptidyl resin, and of reagents to produce batches of activated amino acid solution from the amino acid station (which is not shown), for subsequent supply into the reaction vessels 5.

A (not shown) dimethylformamide (DMF) solvent supply is also part of the supply station 3 and is connected to the system behind the point in the reaction solution supplier assembly 22 connected to a line from the nitrogen gas bomb. The DMF solvent is used both for washing out the reaction vessel 5 itself, and for washing the peptide product produced in batch stages of the coupling procedure and sustained on the filter 10; wherein the elongating protected peptides remain bound to the resin particulates until the final (protected or deprotected) product is cleaved for purification. Wash ports 23 are a further component of the supply station 3, and receive the supplier assembly 22 when washing solvent is flushed through to clean it.

The drainage device 4 is connectable with the drainage port 8 of the reaction vessel 5, and includes an effluent path 25 and a nitrogen gas feed line 26. The drainage port 8 is alternatively connectable with the effluent path 25 or the nitrogen gas feed line 26 through operation of an exchange valve 27.

Prefatorily in connection with the function and effect of the embodiment, a peptide synthesizing procedure of the aforementioned solid-phase peptide synthesizing apparatus 1 is next briefly described, to explain how synthetic peptidyl resin is produced in the reaction vessel 5.

First, a quantity of powdered particulate resin is supplied onto the filter 10 of the reaction vessel 5. After linkage of the carboxyl ends of the initial α-aminos to the resin support, the N-α protecting groups of N-terminus ends thereof are deprotected (deblocked). A solution of coupling reagents, e.g. a mixture of preactivated acyl component (generally, protected amino acid) and dimethylformamide (DMF) solvent, is then supplied into the reaction chamber 11 via the supplier assembly 22 from the reagent tanks 24, according to a protocol of the peptide synthesizing apparatus. In subsequent deprotecting, coupling and washing steps, nitrogen gas is forcibly introduced into the reaction chamber 11 through the gas feed line 26 and the drainage port 8 into the reaction chamber 11, regulated by the exchange valve 27 according to the protocol. The supplied inert gas spouts out from the filter 10, bubbling and thereby stirring the reagent solution as well as the resin support matrix, now anchoring the peptides-in-formation as contained in the reaction chamber 11.

Washing solvent (DMF) is supplied during washing processes between coupling cycles, and deprotecting steps therein, as well as following the final coupling cycle of the peptide synthesis. The washing solvent is supplied into the reaction chamber 11 through supply opening 5a, further according to the protocol.

At the end of the final cycle of the peptide synthesis procedure, the final-coupled amino residue is deblocked of its protecting groups, or, as required, left in the N-α protected condition (in which it remains in one coupling chemistry, since the acidity of the cleavage solution used in the cleavage process described below does not affect the protecting group). Then the synthesized elongate peptides, in peptidyl resin form, are given a final wash with dimethylformamide, methanol, and an ether, in that order; and the washing solvents are flushed through the drainage port 8 of the reaction vessel 5. Nitrogen gas is then forcibly introduced into the reaction chamber 11 through the supply opening 5a in order to dry the protective peptidyl resin of the washing reagents.

In order to obtain the synthetic peptide product in final form, the resultant side chain-protected (and optionally terminal-end protected) peptidyl resin is cleaved in a "cleavage cocktail," which both removes side-chain protecting groups, and liberates the peptides from the resin support particulates in cleaving the chain-anchoring handles, leaving the peptides soluble into the cleavage cocktail.

The cleavage procedure is carried out with the cleavage apparatus 2. Initially, the supplier assembly 22 and the drainage device 4 are detached from the reaction vessel 5, and the drainage port 8 of the reaction vessel 5 is sealed by the cap 9. As indicated in FIG. 4, the reaction vessel 5 is then inserted into a centrifuge tube 28, wherein it is supported on the rim of the tube 28 by the flange 7. The centrifuge tube 28 is then in turn stood in a rack 30. The rack 30 comprises a table disc 31, having radially arranged hemispherical support depressions 31a, and a stand disc 32, concentrically interconnected with the table disc 31, wherein retaining holes 32a radially perforating the stand disc 32 are aligned over the depressions 31a. Thus the centrifuge tube 28 stands in a depression 31a, retained by the edge of the corresponding hole 32a.

Next, the cleavage cocktail is added into the reaction chamber 11 of the reaction vessel 5 through the supply opening 5a with a microsyringe or the like; and the reaction vessel 5 is then stood as it is for a prescribed duration, in order to allow the cocktail time to cleave the elongate synthetic peptides from the insoluble resin support matrix, whereupon the peptides become soluble into the cocktail. With the drainage port 8 capped off, pressure balance is such that surface tension of the meniscus of peptidyl cleavage cocktail just entering the port is maintained, restraining the solution against gravity from travelling further down the drainage port 8 toward the cap 9.

After the process of treatment with the cleavage cocktail, the reaction vessel 5 is withdrawn from the centrifuge tube 28, and the cap 9 is detached from the drainage port 8. The reaction vessel 5 is then reinserted into the centrifuge tube 28. Subsequently, the rubber Jet-fitting 20 on the pressure gun 13 is inserted into the supply opening 5a, and the fit is welded by sufficiently pressing the pressure gun 13 toward the reaction vessel 5. Then by activating the trigger 21 the nozzle valve opens, releasing nitrogen gas under pressure regulated by the main body 12 pressure governor and set to a suitable value with the controller 14. The inert gas is thus blown through the jet fitting 20 and thereby pressurizes the reaction chamber 11, purging it of the cleavage cocktail containing the peptidyl solute, forcibly passing the solution via the filter 10 through the drainage port 8 and into the centrifuge tube 28, wherein the peptidyl solution is a filtrate, and the resin is left behind, retained on the filter 10 in the reaction chamber 11.

Cold diethylether is next added into the centrifuge tube 28 in order to isolate the peptide product from the peptidyl cocktail filtrate. Upon precipitation, the suspension is centrifuged, dividing it into peptide and supernatant. The supernatant is then decanted from the centrifuge tube 28, yielding peptide precipitate.

Therein the peptide precipitate remains wet with ether; and in lieu of open-air evaporative drying, which risks contamination and oxidation of the peptide product, the precipitate Is desiccated with the blow unit 6. To do so, the rubber jet-fitting 20 of the blow unit 6 is replaced with the needle tube 20a. The needle tube 20a is inserted into the centrifuge tube 28, and the trigger 21 is activated in order to spray a stream of nitrogen gas locally onto the peptide precipitate, focused such that the precipitate does not get blown away. Thus the peptide product is bathed in inert gas, which helps to prevent oxidation and at the same time dries it efficiently and rapidly of ether, removing scavenger which has cleansed the peptide of non-peptidyl material, without loss of the product.

Accordingly, utilizing the inventive peptide isolation apparatus 2, there is no mechanical transfer of resin particulate-anchored peptide chains from the reaction vessel 5 into any other containers. Transfer to the centrifuge tube is only after the synthesized peptide chains have become soluble into the cleavage cocktail, which in the preferred embodiment is carried out within the reaction vessel 5 itself, enabled by plugging the drainage port 8 with the cap 9. In particular, the transfer is liquid-phase. The blow unit 6 expels the peptidyl cocktail through the narrow drainage port 8, which otherwise would permit the solution to flow out only quite slowly after the cap 9 is removed. Furthermore, the blow unit 6 greatly speeds drying (as opposed to unassisted evaporation) of the ether-wetted peptide, which remains after precipitation from the peptidyl cocktail and final isolation by centrifuging and decanting of the supernatant.

In sum, mechanical loss of peptidyl resin is practically eliminated, and in small scale peptide synthesis requiring micro-mole regulation, accuracy is ensured. Furthermore, occurrences of cross-vessel contamination, contamination from scavenger, and oxidation of the peptide product are greatly checked. Synthetic peptides of high purity are efficiently yielded through the apparatus, employed in conjunction with a solid-phase peptide synthesizing machine.

Various details of time invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. An apparatus for isolation of a synthetic peptide, for use with a multiple-channel solid phase peptide synthesizing device wherein elongated peptides synthesized in amino-acid coupling stages are linked to an insoluble particulate support matrix in a solid phase of synthetic peptide production, said apparatus comprising:

at least one reaction vessel, said reaction vessel comprising a reaction chamber having a supply opening with a flange at one end thereof and a drainage port at another end thereof, and a filter covering said drainage port which is impermeable to said support matrix, wherein said solid-phase peptide synthesis is performed in said reaction chamber;

means for opening and closing said drainage port operatively connected to said reaction vessel, said means for opening and closing said drainage port comprising a removable stopper;

means for supporting said reaction vessel by said flange operatively connected to said reaction vessel, said means for supporting said reaction vessel comprising a tube into which said reaction vessel is insertable and which has a support opening at one end;

means for supplying inert gas under regulatable pressure into said reaction chamber through said supply opening thereby forcing a liquid phase of a peptide product past said filter and through said drainage port, operatively connected to said reaction vessel, said means for supplying inert gas under regulatable pressure comprising a blow unit removably engageable with said flanged supply opening of said reaction vessel.

2. An apparatus according to claim 1, further comprising
a stand rack for retainably supporting said tube into which said reaction vessel is insertable.

3. An apparatus according to claim 2, wherein said blow unit comprises:

a main housing having a pressure governor and a controller therein, said pressure governor being adjustable through said controller, said main housing having a gas inlet means for connection to a first pressurized inert gas source, and a gas outlet means for allowing gas from said first pressurized inert gas source for releasing pressurized inert gas from said main housing;

a pressure gun for connection to said gas outlet means, said pressure gun including a grip having a gas flow passage therein, and a nozzle in communication with said gas flow passage, and a valve disposed between said gas flow passage and said nozzle for controlling gas flow, said pressure gun also including a trigger for opening and closing said valve; and a pliable jet-fitting removably connected to said nozzle, said jet-fitting configured for insertion into said reaction vessel supply opening wherein an airtight seal between said jet-fitting and said supply opening is provided when said jet-fitting is inserted therein, such that when said trigger is activated to open said nozzle valve, and said reaction chamber is pressurized to be purged of said cleavage solution when said stopper is removed from said drainage port, thereby passing the solution through the filter and the drainage port into the centrifuge tube, in which the peptide product is subsequently precipitated by the addition of a precipitating agent, essentially no gas or peptide product escapes through said airtight seal.

4. An apparatus according to claim 2, wherein said blow unit comprises:

a main housing having a pressure governor and a controller therein, said pressure governor being adjustable through said controller, said main housing having a gas inlet means for connection to a pressurized inert gas source, and a gas outlet means for allowing gas from said pressurized inert gas source for releasing pressurized inert gas from said main housing;

a pressure gun for connection to said gas outlet means, said pressure gun including a grip having a gas flow passage therein, and a nozzle in communication with said gas flow passage, and a valve disposed between said gas flow passage and said nozzle for controlling gas flow, said pressure gun also including a trigger for opening and closing said valve;

a needle tube removably connected to said nozzle of said pressure gun, with an opposite end of said needle tube being configured to exhaust a stream of said pressurized inert gas when said trigger opens said valve of said pressure gun, such that said stream of pressurized gas locally desiccates said precipitated peptide product, thereby expediting evaporation of said precipitating agent and preventing oxidation of said peptide product, said stream of pressurized gas ceasing when said trigger closes said valve.

5. An apparatus according to claim 3, further comprising a second pressurized gas source engageable with said reaction, such that a pressurized gas enters said reaction chamber to effect mixing agitation of reaction solutions used in said synthetic peptide production, and for drying said synthesized peptides in said reaction vessel prior to said cleavage.

* * * * *